(12) United States Patent
Bogdanović et al.

(10) Patent No.: US 6,749,778 B2
(45) Date of Patent: Jun. 15, 2004

(54) PROCESS FOR THE SYNTHESIS OF ORGANOMAGNESIUM COMPOUNDS USING CATALYSTS

(75) Inventors: Borislav Bogdanović, Mülheim an der Ruhr (DE); Manfred Schwickardi, Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/809,575

(22) Filed: Mar. 15, 2001

(65) Prior Publication Data

US 2002/0161229 A1 Oct. 31, 2002

(51) Int. Cl.$^7$ .................................. C07F 3/02
(52) U.S. Cl. .................................. 260/655 G
(58) Field of Search ...................... 260/655 G

(56) References Cited

U.S. PATENT DOCUMENTS

| | | | |
|---|---|---|---|
| 2,777,885 A | * | 1/1957 | Ramsden et al. |
| 5,550,093 A | * | 8/1996 | Wan et al. ............... 502/74 |
| 5,650,528 A | * | 7/1997 | Frey et al. ............... 556/22 |
| 6,096,936 A | * | 8/2000 | Fukunaga et al. ......... 585/419 |
| 6,117,372 A | * | 9/2000 | Bogdanovic et al. ... 260/665 G |
| 6,221,285 B1 | | 4/2001 | Bogdanović et al. ..... 260/665 G |
| 6,303,093 B1 | | 10/2001 | Bogdanović et al. ......... 423/439 |

FOREIGN PATENT DOCUMENTS

DE 19628159 * 1/1998

OTHER PUBLICATIONS

CA:76:121246 abs of Zavod Lab by Fedoseev et al 37(12) pp 1424–5 1971.*
CA:77:164789 abs of J Amer. Chem. Soc. by Rieke et al 94(20) pp 7178–9 1972.*
CA:114:42844 abs of J Org. Chem. by Baker et al 56(2) pp 698–703 1991.*
CA:80:133523 abs of J Amer. Chem. Soc. by Rieke et al 96(6) pp 1775–81 1974.*
Bogdanovic et al., *Angew. Chem. Int. Ed.,* 39:4610–4612 (2000).

* cited by examiner

*Primary Examiner*—Jean F. Vollano
(74) *Attorney, Agent, or Firm*—Norris McLaughlin & Marcus PA

(57) ABSTRACT

A process for the preparation of organomagnesium compounds from organic halides and magnesium metal in the presence of transition metal catalysts using an activity-enhancing main group metal component. The latter is a compound of a metal of Periodic Table groups 1, 2 or 13 in which elements of Periodic Table groups 14–17 or hydrogen are bonded to the metal. Some of these additional components may also be formed in situ.

22 Claims, No Drawings

PROCESS FOR THE SYNTHESIS OF ORGANOMAGNESIUM COMPOUNDS USING CATALYSTS

The present invention relates to an improved process for the preparation of organomagnesium compounds from organohalides and magnesium metal in the presence of transition metal catalysts and an activity-enhancing main group metal component.

PRIOR ART

Grignard compounds are usually prepared by reacting organic halides with magnesium in an ethereal solvent; in certain cases, they can also be prepared in hydrocarbons (Comprehensive Organometallic Chemistry II, Vol. 1, 1995, p. 58–63; Comprehensive Organometallic Chemistry I, Vol. 1, 1982, p. 155; Chem. Ber. 1990, 123, 1507 and 1517; Houben-Weyl, Methoden der organischen Chemie, 1973, 13/2a, 53–192).

However, there is a wide variety of organic halogen compounds, including, in particular, aromatic, vinylic and heterocyclic chloro compounds, with which the Grignard reaction proceeds hesitantly, with low yields, poorly or not at all. For increasing the reactivity of magnesium towards such halides, numerous methods are known which are based on physical (grinding, ultrasonication, metal vaporization) or chemical (entrainment method, Rieke method, dehydrogenation of magnesium hydride, reversible formation of magnesium anthracene) activation of magnesium (Active Metals—Preparation, Characterization, Applications, A. Fürstner (Ed.), Verlag Chemie, 1996). Further, a process for the preparation of Grignard compounds is known which is based on the physical and chemical activation of the magnesium metal employed (DE 27 55 300 A1, Schering A G). Thus, prior to performing the Grignard reaction, the magnesium metal is ground in the presence of organometallic aluminum, boron or zinc compounds in which the organo groups may also be partly substituted by halogens, hydrogen or alkoxy groups, and after the addition of organomagnesium compounds, it is converted to the corresponding Grignard compounds without further grinding with organyl halides. As catalysts for the Grignard reaction, anthracene or magnesium anthracene and their derivatives are known; however, they can be employed only in the case of allyl, propargyl and benzyl halides (Chem. Ber. 1990, 123, 1507). There are drawbacks in the mentioned methods in that they are either relatively tedious and expensive or subjected to limitations in application or effectiveness, or result in an increased consumption of magnesium (entrainment method: J. Org. Chem. 1959, 24, 504). Therefore, there is still a need for effective and economical methods for the preparation of Grignard compounds from the above mentioned inert organic halogen compounds which are not subject to the mentioned draw-backs, and with the proviso that conventional, commercially available magnesium grades can be used.

According to the Patent Application PCT/WO 98/02443 filed by the Studiengesellschaft Kohle, which corresponds to U.S. Ser. No. 09/214,369, filed Jan. 5, 1999, a process for the preparation of Grignard compounds is known which is characterized in that organic halides are reacted with magnesium metal in an ethereal solvent in the presence of catalysts consisting of inorganic Grignard reagents of transition metals having the general formula $[M(MgX)_m(MgX_2)_n]_2$, wherein M is a transition metal of Periodic Table groups 4–10, X is a halogen, m=1, 2, 3, n=0–1, and optionally anthracene or substituted anthracenes or their Mg adducts and/or magnesium halides as cocatalysts. Iron halides and manganese halides are considered the preferred catalyst components according to the mentioned process. A preferred mode of carrying out the process involves performing the reaction of organic chlorine compounds with magnesium powder in the presence of catalysts prepared from iron or manganese halides, 9,10-diphenylanthracene, magnesium halide and excess Mg powder in THF, monoglyme or diglyme.

According to the Patent Application PCT/EP 98/08056 filed by the Studiengesell-schaft Kohle mbH, which corresponds to U.S. Ser. No. 09/581,874, filed Jun. 19, 2000, transition metal compounds in which elements of groups 15 or 16 (preferably N or O) are bonded to the transition metal are also suitable catalysts. Particularly preferred are those transition metal catalysts which contain Fe, Mn, Co and Cu bound to alkoxy, aryloxy, amido and phthalocyanine groups.

DESCRIPTION OF THE INVENTION

Surprisingly, it has now been found that the catalytic activity of the transition metal catalysts in which one or more elements selected from groups 14, 15, 16 or 17 are bonded to a metal selected from the metals of groups 3, 4, 5, 6, 7, 8, 9, 10 or 11 can be significantly improved by the addition of a main group metal component (Angew. Chem. 2000, 112, No. 24, 4788–4790). For this purpose, compounds of main group metals of Periodic Table groups 1, 2 and 13 (especially Li, Na, Mg, Al or B) are used in which one or more elements of Periodic Table groups 14, 15, 16 or 17 (especially C, N, O or halogens) or hydrogen are bonded to the metal. The main group metal additional components according to the invention are preferably employed in the form of alkyl, aryl, alkoxy, aryloxy, alkylamido, arylamido, phthalocyanine, halogen and/or hydrogen compounds. Some of these additional components may also be formed in situ (such as RMgX, formed from RX, where R is an alkyl or aryl residue and X is a halogen atom, and Mg metal, being present in excess). The said alkyl, alkoxy or alkylamido compounds are preferably employed with a chain length of from $C_1$ to $C_{16}$, whereas the aryl, aryloxy or arylamido compounds are preferably employed as phenyl compounds or substituted compounds of this kind, and the halogens are preferably employed in the form of chlorine, bromine or iodine.

The transition metal catalyst comprises a transition metal selected from Periodic Table groups 3, 4, 5, 6, 7, 8, 9, 10 or 11, and one or more elements selected from groups 14, 15, 16 or 17 bonded to the transition metal. The transition metal catalyst, for example, contains Fe, Mn, Co or Cu.

The additional main group metal component used according to the present process includes, for example, Grignard compounds (such as EtMgCl, phenyl-MgCl), diorganomagnesium compounds (such as diethylmagnesium), magnesium hydride, HMgCl, organomagnesium alcoholates (such as phenyl-MgOEt), magnesium phthalocyanine, lithium hydride, Li, Na, Al or B organyls (such as triethylaluminum, butyllithium, triphenylboron) as well as diorganoaluminum hydride and chloride (such as diisobutylaluminum hydride or diethylaluminum chloride).

The main group metal additional components of the present process (e.g. $AlEt_3$ and EtMgBr) alone do not cause catalysis of the Grignard reaction (Example 9, Comparative Examples); however, when used together with the transition metal compounds mentioned, enhanced catalytic effects are observed.

The catalyst components according to the invention reduce the transition metal compound into a form which is particularly active catalytically. Thus, they do not function as mere magnesium metal activation agents (such as the organoaluminum, organoboron or organozinc compounds in DE 27 55 300 A1, Schering A G), but they are chemical reactants in the preparation of particularly active transition metal catalysts (see Examples 1, 2, 9, and Comparative Examples), where they are consumed partially or completely. Thus, for example, ferrous chloride will react with the organomagnesium compound n-heptylmagnesium bromide with reduction of the iron and release of heptane and heptene to yield a particularly active catalyst.

Also, it was found that, in addition to the catalysts of transition metals described in PCT/WO 98/02443 and PCT/EP 98/08056, organometallic compounds of these elements, such as metallocenes, e.g. ferrocene, and substituted metallocenes can also be used as catalysts for Grignard synthesis.

The magnesium metal is employed in the form of commercially available powders, dusts, raspings, granules, chips or turnings (preferably as a powder). If necessary, the magnesium metal may be employed in an activated form or be continuously activated superficially, while the reaction is performed, using agitating, grinding or cutting devices (Example 3).

In addition, halides of Periodic Table 1st and 2nd main group metals (preferably Li and Mg) as well as ammonium halides and organoammonium halides, such as $MgCl_2$, LiCl or $NBu_4Br$, can be employed as cocatalysts. Magnesium halides, when used as cocatalysts, can also be generated in situ by the addition of, for example, 1,2-dihaloethane to the magnesium, which is present in excess (Example 5).

Anthracene and substituted anthracene compounds, especially 9,10-disubstituted anthracenes (preferably 9,10-diphenylanthracene), or their magnesium adducts can be used as further cocatalysts (Example 17). Anthracene has the specific property of dissolving magnesium metal. Magnesium anthracene, which is produced thereby, can readily release its magnesium atom in Grignard reactions to regenerate anthracene, which can then again dissolve magnesium metal. Thus, anthracene and some substituted anthracenes, especially 9,10-diphenylanthracene, in catalytic amounts can provide "quasi-soluble magnesium" and thus function as phase-transfer catalysts (Accounts of Chem. Res., 21, 261–267 (1988); Chem. Ber. 123 (1990), 1529–1535).

The process is preferably performed in ethereal solvents (especially THF, diglyme and monoglyme), preferably at room temperature and up to the boiling temperature of the solvent; due to the high activity, the reactions may also be performed at lower temperatures.

A preferred, simplified mode of performing the present process involves the use of the main group metal compound, required to enhance the activity of the transition metal compound (e.g. ferrous halide), in the form of a Grignard compound. The latter may also be formed in situ from an organohalogen compound and the Mg metal, which is present in excess. The organohalogen compounds are preferably used as alkyl or aryl halides; alkyl compounds having a chain length of from $C_1$ to $C_{16}$ and aryl groups in the form of phenyl groups or substituted compounds of this kind being preferred. In particular, the halogens are employed in the form of chlorine, bromine or iodine. The molar ratio of the organohalogen compound to the transition metal catalyst is >0.2:1, preferably between 1 and 5:1.

The inventive process leads to significantly higher catalyst activity as compared to the known processes. The use of the additional main group metal compound which reduces the transition metal component into a particularly active form enables even particularly difficult Grignard syntheses to be realized in high yields.

In particular, the synthesis of hardly accessible Grignard compounds from aromatic chlorine compounds, such as chlorobenzene and chlorine-containing condensed aromatics, such as chloronaphthalene, chloroanthracene and chlorophenanthrene, or substituted compounds of this kind having substituents consisting of alkyl, aryl, alkoxy, aryloxy, alkylamido and/or arylamido groups, and chlorine-containing heterocycles, especially aromatic chloroheterocycles with N, O or S heteroatoms, such as chloropyridine, chloroquinoline, chloropyrrole and chlorofurane or substituted compounds of this kind having substituents consisting of alkyl, aryl, alkoxy, aryloxy, alkylamido and/or arylamido groups, can be significantly improved according to the process of this invention.

The performance of the catalysis according to the invention is illustrated by examples involving particularly difficult reactions, namely the conversions of acetal-protected chlorobenzaldehyde (Examples 1–14), 5-chlorobenzodioxole (Examples 1s and 17) and 2-chloro-6-methoxypyridine (Example 16) to the corresponding Grignard compounds.

Using a Grignard reaction which could be performed only with low yields to date, namely the preparation of the Grignard compound of 4-chlorobenzaldehyde diethyl acetal, the dependence of the product yield on the quantity of main group metal used is clearly demonstrated for EtMgBr (preparation from EtBr in situ) as an example (Examples 1 and 2). In the mentioned processes of the Studiengesellschaft Kohle mbH, a maximum of 4 drops of ethyl bromide is employed for etching the Mg surface (Pearson, Cowan, Becker, J. Org. Chem. 24, 504, 1959). However, if 4 mol of EtBr is used per mole of ferrous chloride, the yield of isolated Grignard compound is 85% of theory (Example 2), whereas a Grignard yield of only 45% of theory is achieved when 0.2 mol of EtBr is used per mole of ferrous chloride (by analogy with PCT/WO 98/02443 and PCT/EP 98/08056) under the same conditions (Example 2, Comparative Example).

For the catalytic preparation of the Grignard compounds of 5-chloro-1,3-benzodioxole (Example 15) and 2-chloro-6-methoxypyridine (Example 16), it was also established that significantly higher Grignard yields can be achieved when a significantly higher amount of ethyl bromide is employed as compared with the known processes.

| Educt | EtBr:Fe = 0.2:1 in accordance with PCT/WO 98/02443 and PCT/EP 98/08056 | EtBr:Fe = 2.2:1 | EtBr:Fe = 4:1 |
|---|---|---|---|
| 4-chlorobenzaldehyde diethyl acetal (Example 2) | 45% yield[1] (after 16 h) | | 85% yield[1] (after 16 h) |

-continued

| Educt | EtBr:Fe = 0.2:1 in accordance with PCT/WO 98/02443 and PCT/EP 98/08056 | EtBr:Fe = 2.2:1 | EtBr:Fe = 4:1 |
|---|---|---|---|
| 5-chloro-1,3-benzodioxide (Example 15) | 39.8% yield (after 2.5 h) | 76.4% yield (after 2.25 h) | |
| 2-chloro-6-methoxy-pyridine (Example 16) | 52.1% yield (after 9 h) | 83.2% yield (after 8.75 h) | |

[1])Isolated yield after reaction with chlorotrimethylsilane

An explanation of these facts was provided, inter alia, by examining the centrifuged catalyst solutions for their iron contents. If ferrous chloride in THF at room temperature is added to excess Mg powder and ethylmagnesium bromide (formed in situ from EtBr and Mg), the amount of dissolved Fe increases from 40 to 85% as the EtMgBr content increases.

| | dissolved iron content (reaction time at room temp.: 30 min) |
|---|---|
| 0.2 mol of EtBr per mole of Fe (as in Pat. Appl. PCT/WO 98/02443) | 40% |
| 1 mol of EtBr per mole of Fe | 71% |
| 4 mol of EtBr per mole of Fe | 85% |

The use of the mentioned main group organometallic compounds in the formation of the catalyst in equimolar or higher amounts (as compared to substoichiometric amounts in the Patent Application filed by the Studiengesellschaft Kohle, PCT/WO 98/02443) causes the iron halide to dissolve quickly, for the most part thereof, rather than precipitating in metallic form, which contributes to the formation of a particularly active catalyst system. Ethyl bromide, which was used only in minor amounts in the Patent Application PCT/WO 98/02443 (0.2 mol of EtBr per mole of iron halide) and only served to etch the surface of the Mg particles, is an activity-enhancing component of the present catalyst system when used in equimolar amounts or in excess.

In addition to EtMgBr (prepared in situ), for the first time, Li, Na, Mg, Al and B compounds with hydride, halogen, ethyl, butyl, heptyl, phenyl, alkoxy, aryloxy and phthalo-cyanine groups, inter alia, which can be combined with various transition metal compounds, were also employed for this purpose, e.g.: phenylmagnesium bromide+Co-phthalocyanine (Example 11), butyllithium+FeCl$_2$ (Example 8), AlEt$_3$+FeCl$_2$ (Example 9), or Mg-phthalocyanine+FeCl$_2$ (Example 6). The wide variety of possible catalyst combinations and cocatalysts in the present process offers the possibility of a problem-oriented catalyst design.

The invention is illustrated by way of the following Examples without being limited thereto. The experiments were performed under a protective gas (argon). Anhydrous solvents deprived of air were employed. In all experiments, commercially available Mg powder (270 mesh; i.e. particle size of about 53 μm) was used. For this purpose, anhydrous MgCl$_2$ was prepared from 1,2-dichloroethane and magnesium powder in THF or formed in situ.

EXAMPLE 1

Preparation of the Grignard Compound of 4-Chlorobenzaldehyde Diethyl Acetal with Ethyl Bromide, FeCl$_2$ and MgCl$_2$ (Ethyl Bromide:FeCl$_2$= 1.06:1) and isolation thereof as a TMS Product To 2.0 g (82 mmol) of magnesium powder (270 mesh) in an argon atmosphere were added 10 ml of THF and 0.20 ml (2.68 mmol) of ethyl bromide, and the mixture was stirred at room temperature in a closed apparatus for 2.5 h. Then, 322 mg (2.54 mmol) of anhydrous ferrous chloride, 5.0 ml (2.4 mmol) of an anhydrous 0.485 M magnesium chloride solution in THF and another 10 ml of THF were added, whereupon the reaction mixture spontaneously heated by about 10-15° C. and the solution turned to a deep-brown color. The mixture was subsequently stirred for a total of 3 minutes, followed by adding 10 ml (49.2 mmol) of 4-chlorobenzaldehyde diethyl acetal (97.8%, distilled over NaBH$_4$) dropwise within about 1 hour with vigorous stirring using a magnetic stirring bar. An exothermic reaction immediately occurred, the reaction mixture heating to >40° C. Thereafter, the mixture was stirred at room temperature for another 15 hours to obtain 35 ml of a deep-brown solution which was slightly oily.

In 2 portions, 1.2 ml of chlorotrimethylsilane was added to 5.0 ml of the solution at room temperature, whereupon a slightly exothermic reaction occurred. The mixture was diluted with 5 ml of THF and stirred over night at room temperature. The solvent was subsequently evaporated off in an oil-pump vacuum, and the residue was dried at 20° C./0.1 mbar for 30 min. Then, 20 ml of anhydrous pentane was added, the mixture was stirred, and the suspension obtained was filtered through a D4 frit. The residue on the frit was again washed twice with pentane, and the light brown filtrate was concentrated in an oil-pump vacuum at room temperature to obtain 1.74 g of a brownish oil. According to a gas-chromato-graphical analysis, the oil contained 82.7% of 4-(trimethylsilyl)benzaldehyde diethyl acetal (detection by MS, GC-MS coupling and IR) and 2.06% of educt. Thus, the yield of isolated Grignard compound was 81% of theory.

In a comparative experiment with addition of ethyl bromide, but with no FeCl$_2$ and MgCl$_2$, the Grignard yield was <6%.

EXAMPLE 2

Preparation of the Grignard Compound of 4-Chlorobenzaldehyde Diethyl Acetal with Ethyl Bromide, FeCl$_2$ and MgCl$_2$ (Ethyl Bromide:FeCl$_2$= 4.0:1) and isolation thereof as a TMS Product.

The experiment was conducted by analogy with Example 1, 10 mmol of ethyl bromide instead of 2.68 mmol being used. From the isolated TMS product, the Grignard yield was 85% of theory.

In a comparative experiment with addition of only 0.54 mmol of ethyl bromide (ethyl bromide:FeCl$_2$=0.2:1), the Grignard yield was 45% of theory as determined from the isolated TMS product.

EXAMPLE 3

Preparation of the Grignard Compound of 4-Chlorobenzaldehyde Diethyl Acetal with Ethyl Bromide, FeCl$_2$ and MgCl$_2$ (Ethyl Bromide:FeCl$_2$= 2.1:1) Under the Action of Grinding Media In an argon atmosphere, 16 g (658 mmol) of magnesium powder (270 mesh) was stirred with 200 ml of THF together with glass spheres (diameter=5 mm) in a 1-liter four-necked round-bottom flask equipped with a reflux condenser, metal-blade agitator, screw-operated dropping funnel, thermocouple and argon inlet. The glass spheres were thereby whirled up to obtain a grinding effect. Then, 2 times 2.0 ml (53.6 mmol) of ethyl bromide (dried over molecular sieve) was added, each time causing an exothermic reaction. The mixture was ground at room temperature for 2 h, followed by adding 3.21 g (25.3 mmol) of anhydrous ferrous chloride and 50 ml (24.3 mmol) of a 0.485 M anhydrous $MgCl_2$ solution in THF, argon being passed over. A deep-brown solution was formed with an exotherm; it was stirred or ground for a total of 5 min. Then, 100 ml (492 mmol) of 4-chlorobenzaldehyde diethyl acetal (97.8%) was added dropwise to the reaction mixture within 60 minutes, which caused a spontaneous exotherm. During the dropwise addition, the reaction mixture was maintained at temperatures of between 35 and 45° C. by temporary external cooling, and only gradually cooled down to room temperature spontaneously after the end of the addition. The reaction mixture was ground for a total of 11 h to obtain a deep-brown solution which was slightly oily.

To an aliquot of the reaction solution segregated from the excess magnesium, 2 M HCl was added in tert.-butyl methyl ether, followed by stirring for 1 h, and the organic phase was examined by gas chromatography. The sample contained 92.0% of benzaidehyde and 3.4% of 4-chlorobenzaldehyde (evaluation without solvent).

EXAMPLE 4

Preparation of the Grignard Compound of 4-Chlorobenzaldehyde Diethyl Acetal with Bromobenzene, $FeCl_2$ and $MgCl_2$ and isolation thereof as a TMS Product The experiment was conducted by analogy with Example 1, bromobenzene being used instead of ethyl bromide. From the isolated TMS product, the Grignard yield was 74%.

EXAMPLE 5

Preparation of the Grignard Compound of 4-Chlorobenzaldehyde Diethyl Acetal with Heptyl Bromide, $FeCl_2$ and 1,2-Dichloroethane (for the Preparation of $MgCl_2$ in Situ) and isolation thereof as a TMS Product The experiment was conducted by analogy with Example 1, n-heptyl bromide being used instead of ethyl bromide and 1,2-dichloroethane+5 ml of THF being used instead of the $MgCl_2$ solution. From the isolated TMS product, the Grignard yield was 76%.

EXAMPLE 6

Preparation of the Grignard Compound of 4-Chlorobenzaldehyde Diethyl Acetal with Phthalocyanine Mg Complex, $FeCl_2$ and $MgCl_2$ and isolation thereof as a TMS Product.

The experiment was conducted by analogy with Example 1, 1.88 mmol of phthalocyanine Mg complex being used instead of ethyl bromide. From the isolated TMS product, the Grignard yield was 71%.

EXAMPLE 7

Preparation of the Grignard Compound of 4-Chlorobenzaldehyde Diethyl Acetal with Diethyl Magnesium, $FeCl_2$ and $MgCl_2$ and isolation thereof as a TMS Product The experiment was conducted by analogy with Example 1, 1.31 mmol of diethylmagnesium being used instead of ethyl bromide. From the isolated TMS product, the Grignard yield was 77%.

EXAMPLE 8

Preparation of the Grignard Compound of 4-Chlorobenzaldehyde Diethyl Acetal with n-Butyllithium, $FeCl_2$ and $MgCl_2$ and isolation thereof as a TMS Product The experiment was conducted by analogy with Example 1, 5.0 mmol of butyllithium being used instead of ethyl bromide. From the isolated TMS product, the Grignard yield was 72%.

EXAMPLE 9

Preparation of the Grignard Compound of 4-Chlorobenzaldehyde Diethyl Acetal with Triethylaluminum, $FeCl_2$ and $MgCl_2$ and isolation thereof as a TMS Product The experiment was conducted by analogy with Example 1, 3.3 mmol of triethylaluminum being used instead of ethyl bromide. From the isolated TMS product, the Grignard yield was 70%.

a) In a comparative experiment with addition of triethylaluminum, but with no $FeCl_2$ and $MgCl_2$, the Grignard yield was 4%.

b) In a comparative experiment with addition of 2.7 mmol of ethyl bromide and 3.3 mmol of triethylaluminum, but with no $FeCl_2$ and $MgCl_2$, the Grignard yield was 4%.

c) In a comparative experiment with addition of 2.7 mmol of ethyl bromide, 3.3 mmol of triethylaluminum and 2.4 mmol of MgCl2, but with no FeCl2, the Grignard yield was 5%.

EXAMPLE 10

Preparation of the Grignard Compound of 4-Chlorobenzaldehyde Diethyl Acetal with Bromobenzene, $MnCl_2$ and $MgCl_2$ and isolation thereof as a TMS Product The experiment was conducted by analogy with Example 1, bromobenzene being used instead of ethyl bromide and $MnCl_2$ being used instead of $FeCl_2$. From the isolated TMS product, the Grignard yield was 69%.

EXAMPLE 11

Preparation of the Grignard Compound of 4-Chlorobenzaldehyde Diethyl Acetal with Bromobenzene and Cobalt Phthalocyanine and isolation thereof as a TMS Product The experiment was conducted by analogy with Example 5, cobalt phthalocyanine being used instead of $FeCl_2$ and 5 ml of THF being used instead of the $MgCl_2$ solution. From the isolated TMS product, the Grignard yield was 59%.

EXAMPLE 12

Preparation of the Grignard Compound of 4-Chlorobenzaldehyde Diethyl Acetal with Ethyl Bromide, Iron(II) Ethanolate and $MgCl_2$ and isolation thereof as a TMS Product.

The experiment was conducted by analogy with Example 1, iron(II) ethanolate being used instead of $FeCl_2$. From the isolated TMS product, the Grignard yield was 69%.

EXAMPLE 13

Preparation of the Grignard Compound of 4-Chlorobenzaldehyde Diethyl Acetal with Ethyl Bromide and FeCl$_2$ without a Cocatalyst and isolation thereof as a TMS Product.

The experiment was conducted by analogy with Example 2, 5 ml of THF being used instead of the MgCl$_2$ solution. From the isolated TMS product, the Grignard yield was 71%.

EXAMPLE 14

Preparation of the Grignard Compound of 4-Chlorobenzaldehyde Diethyl Acetal with Ethyl Bromide, FeCl$_2$ and LiCl and isolation thereof as a TMS Product The experiment was conducted by analogy with Example 2, anhydrous lithium chloride being used as the cocatalyst instead of MgCl$_2$. From the isolated TMS product, the Grignard yield was 80%.

EXAMPLE 15

Preparation of the Grignard Compound of 5-Chloro-1,3-Benzodioxole with Ethyl Bromide, FeCl$_2$ and MgCl$_2$ (Ethyl Bromide:FeCl$_2$=2.2:1)

To 1.12 g (46.1 mmol) of magnesium powder (270 mesh) in an argon atmosphere were added 14 ml of THF and 0.28 ml (3.75 mmol) of ethyl bromide, and the mixture was stirred at room temperature for 1 h. Then, 220 mg (1.74 mmol) of anhydrous ferrous chloride and 3.5 ml (1.7 mmol) of 0.485 M MgCl$_2$ solution in THF were added, and the mixture was stirred for 3 minutes with a magnetic stirring bar, whereupon the solution turned to a deep-brown color. Then, 4.1 ml (34.4 mmol) of 5-chloro-1,3-benzodioxole (98%) was added dropwise within 1 h which caused the reaction mixture to heat briefly from 22° C. to a maximum of 52° C.

The course of the reaction was followed by taking samples. Thus, aliquots of the reaction mixture were hydrolyzed in tert.-butyl methyl ether, and the organic phase was examined by gas chromatography. The identification of the reaction product was effected by GC-MS coupling and silanization of the Grignard compound with chlorotrimethylsilane and detection of the TMS product, also by a GC-MS coupling.

Course of the reaction: After 2¼ h: 76.4%, after 8½ h: 80.7%, and after 23¼ h: 82.9% of Grignard yield.
  a) In a comparative experiment (with addition of only 0.35 mmol of ethyl bromide; ethyl bromide: FeCl$_2$=0.2:1), the Grignard yield was 39.8% after 2.5 h.
  b) In a comparative experiment (with addition of ethyl bromide to etch the magnesium), but with no FeCl$_2$ and MgCl$_2$, a Grignard yield of only 1.3% was obtained after a reaction time of 38½ h at room temperature.

EXAMPLE 16

Preparation of the Grignard Compound of 2-chloro-6-methoxypyridine With Ethyl Bromide, FeCl$_2$ and MgCl$_2$ (ethyl bromide:FeCl$_2$=2.2:1)

The experiment was conducted by analogy with Example 15, 2-chloro-6-methoxypyridine instead of 5-chloro-1,3-benzodioxole being reacted with magnesium. The temperature of the reaction mixture, which temporarily increased due to the reaction heat, was limited to a maximum of 45° C. by external cooling.

Course of the reaction: After 2½ h: 62.4%, after 8¾ h: 83.2%, and after 23½ h: 95.9% of Grignard yield.
  a) In a comparative experiment (with addition of only 0.35 mmol of ethyl bromide; ethyl bromide:FeCl$_2$=0.2:1), the Grignard yield was 37.4% after 2.5 h and 52.1% after 9 h.
  b) In a comparative experiment (with addition of ethyl bromide to etch the magnesium), but with no FeCl$_2$ and MgCl$_2$, a Grignard yield of only 12.8% was obtained after a reaction time of 29¾ h at room temperature.

EXAMPLE 17

Preparation of the Grignard Compound of 5-chloro-1,3-benzodioxole With Ethyl Bromide, 9,10-diphenylanthracene, FeCl$_2$ and MgCl$_2$ The experiment was conducted by analogy with Example 15, 135 mg (0.41 mmol) of 9,10-diphenylanthracene being additionally added to the weighed-in magnesium. The Grignard yield was 85.2% after 2¼ h.

What is claimed is:

1. A process for the preparation of a Grignard compound, said process comprising reacting an organic halide and magnesium metal in a solvent in the presence of:
   a) a first metal-containing compound, which is a transition metal catalyst comprising:
      i) a transition metal selected from Periodic Table groups 3, 4, 5, 6, 7, 8, 9, 10 or 11; and
      ii) one or more elements selected from groups 14, 15, 16 or 17 bonded to said transition metal; and
   b) a second metal-containing compound, said second metal-containing compound increasing the activity of said transition metal catalyst, said second metal-containing compound selected from an organomagnesium halide.

2. The process according to claim 1, wherein said organic halide is selected from the group consisting of aromatic chloro compounds, chlorine-containing heterocycles and functioalized aromatic or heterocyclic chlorine compounds.

3. The process according to claim 1, wherein an ethereal solvent is used as said solvent.

4. The process according to claim 3, wherein tetrehydrofuran, monoglyme or diglyme are used as said ethereal solvent.

5. The process according to claim 1, wherein said transition metal catalyst contains Fe, Mn, Co or Cu.

6. The process according to claim 1, wherein one or more elements selected from the group consisting of the elements Cl, Br, I, O, N and C are bonded to said transition metal.

7. The process according to claim 6, wherein C, N or O are bound to the transition metal in the form of an alkyl or aryl group or a metallocene complex, or in the form of an arnide or phthalocyanine, or in the form of an alkoxy or aryloxy group.

8. The process according to claim 1, wherein an iron or manganese halide is used as said transition metal catalyst.

9. The process according to claim 1, wherein said organomagnesium halide is formed in situ from an organic halide and excess magnesium.

10. The process according to claim 9, wherein an alkyl or aryl halogen compound is used as said organic halide.

11. The process according to claim 10, wherein the molar ratio of organic halide to transition metal catalyst is >0.2:1.

12. The process according to claim 11, wherein said molar ratio is at least 1:1.

13. The process according to claim 1, wherein in addition to said first metal-containing compound and said second metal-containing compound one or more cocatalysts are additionally employed.

14. The process according to claim 13, wherein anthracene or a substituted anthracene or an Mg adduct thereof and/or a halide of a Periodic Table $1^{st}$ and $2^{nd}$ main group metal and/or an ammonium halide and/or an organo-ammonium halide are employed as said cocatalyst.

15. The process according to claim 14, wherein an Mg or Li halide is employed as said cocatalyst.

16. The process according to claim 15, wherein a magnesium halide formed in situ is employed as said cocatalyst.

17. The process according to claim 1, wherein the reaction is performed at temperatures of up to the boiling temperature of the solvent employed.

18. The process according to claim 1, wherein said magnesium metal is used in the form of turnings, raspings, granules, chips, dust or powders.

19. The process according to claim 18, wherein said magnesium metal is used as a finely divided powder.

20. The process according to claim 18, wherein said magnesium metal is activated, prior to being used, by grinding, agitating or cutting processes, ultrasonication, heating in a vacuum, or by the addition of activating agents.

21. The process according to claim 20, wherein said magnesium metal is activated by the addition of iodine.

22. The process according to claim 18, wherein said magnesium metal is activated, while the reaction is performed, by grinding, agitating or cutting processes or ultrasonication.

* * * * *

UNITED STATES PATENT AND TRADEMARK OFFICE
CERTIFICATE OF CORRECTION

PATENT NO. : 6,749,778 B2
DATED : June 15, 2004
INVENTOR(S) : Bogdanovic et al.

It is certified that error appears in the above-identified patent and that said Letters Patent is hereby corrected as shown below:

<u>Column 4,</u>
Line 33, "(Examples 1s and 17)" should read -- (Examples 15 and 17) --

Signed and Sealed this

Fourteenth Day of December, 2004

JON W. DUDAS
*Director of the United States Patent and Trademark Office*